United States Patent [19]
Kleemann et al.

[11] 3,931,185
[45] Jan. 6, 1976

[54] 1-PHENYL-2,2,4,4-$C_1$-$C_2$ ALKYL-3-[4-(PHENYL OR PYRIDYL)-PIPERAZINO]-CYCLOBUTANOLS-(1)

[75] Inventors: Manfred Kleemann, Tamm; Joachim Kahling, Biberach, Riss; Gerhart Griss, Biberach, Riss; Rudolf Hurnaus, Biberach, Riss, all of Germany

[73] Assignee: Boehringer Ingelheim GmbH, Ingelheim am Rhein, Germany

[22] Filed: Nov. 6, 1973

[21] Appl. No.: 413,233

[30]    Foreign Application Priority Data
Nov. 11, 1972    Germany............................ 2255439
Oct. 3, 1973     Germany............................ 2349639

[52] U.S. Cl. 260/268 PH; 260/268 BC; 260/268 H; 260/477; 260/479 R; 260/570.5 CA; 424/250
[51] Int. Cl.²..................................... C07D 295/12
[58] Field of Search .... 260/268 H, 268 PH, 268 BC

[56]          References Cited
       FOREIGN PATENTS OR APPLICATIONS
985,815    3/1965    United Kingdom
           OTHER PUBLICATIONS
Burger, Medicinal Chemistry, 2nd Ed., p. 42, (1960).

*Primary Examiner*—Donald G. Daus
*Assistant Examiner*—Jose Tovar
*Attorney, Agent, or Firm*—Hammond & Littell

[57]             ABSTRACT
This invention relates to cyclobutane derivatives having the formula

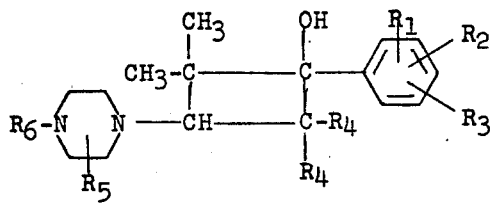

wherein $R_1$ to $R_3$, which may be the same or different, represent hydrogen atoms, halogen atoms, hydroxy, trifluoromethyl, benzyloxy, acyloxy groups, alkyl groups with 1 to 6 carbon atoms, alkoxy groups with 1 to 3 carbon atoms, phenyl, cyclohexyl, or 2 of the radicals $R_1$ to $R_3$ together represents a methylenedioxy group, $R_4$ represents a hydrogen atom or an alkyl group with 1 or 2 carbon atoms, $R_5$ represents a hydrogen atom or an alkyl group with 1 to 3 carbon atoms and $R_6$ represents a phenyl group, which may be mono- or disubstituted by halogen atoms, trifluoromethyl, hydroxy, nitro, amino, benzyloxy, acyloxy groups, alkyl groups with 1 to 3 carbon atoms, alkoxy groups with 1 to 3 carbon atoms or alkylthio groups with 1 to 3 carbon atoms; or a pyridyl group, optionally substituted by a halogen atom, a hydroxy, nitro, amino, benzyloxy, acyloxy, carboxy group, a carbalkoxy group with 1 to 3 carbon atoms in the alkoxy, an alkyl group with 1 to 3 carbon atoms or an alkoxy group with 1 to 3 carbon atoms;

to salts thereof with physiologically compatible inorganic or organic acids or bases as well as to processes for their preparation.

The cyclobutane compounds of the above general formula show valuable pharmacological properties, especially a sedative and muscle relaxing activity.

11 Claims, No Drawings

3,931,185

1-PHENYL-2,2,4,4-$C_1$-$C_2$ ALKYL-3-[4-(PHENYL OR PYRIDYL)-PIPERAZINO]-CYCLOBUTANOLS-(1)

OBJECTS OF THE INVENTION

An object of the present invention is the obtaining of a cyclobutane derivative selected from the group consisting of (1) a compound having the formula I

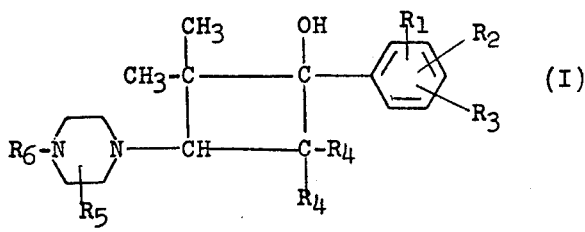

wherein $R_1$, $R_2$ and $R_3$ are members selected from the group consisting of hydrogen, halogen, hydroxy, trifluoromethyl, benzyloxy, alkyl having 1 to 6 carbon atoms, alkoxy having 1 to 3 carbon atoms, acyloxy where acyl is an acyl of an organic carboxylic acid having 1 to 12 carbon atoms, phenyl, cyclohexyl, and any two of $R_1$, $R_2$ and $R_3$ taken together, methylenedioxy, $R_4$ is a member selected from the group consisting of hydrogen and alkyl having 1 to 2 carbon atoms, $R_5$ is a member selected from the group consisting of hydrogen and alkyl having 1 to 3 carbon atoms, and $R_6$ is a member selected from the group consisting of

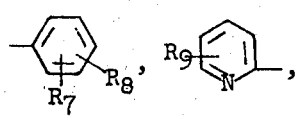

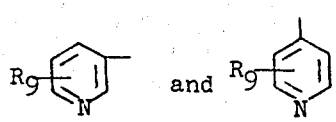

wherein $R_7$ and $R_8$ are members selected from the group consisting of hydrogen, halogen, trifluoromethyl, hydroxy, nitro, amino, benzyloxy, alkyl having 1 to 3 carbons, alkoxy having 1 to 3 carbon atoms, alkylthio having 1 to 3 carbon atoms and acyloxy where acyl is an acyl of an organic carboxylic acid having 1 to 12 carbon atoms, and $R_9$ is a member selected from the group consisting of hydrogen, halogen, hydroxy, nitro, amino, benzyloxy, carboxy, carbalkoxy having 1 to 3 carbon atoms in the alkoxy, alkyl having 1 to 3 carbon atoms, alkoxy having 1 to 3 carbon atoms and acyloxy where acyl is an acyl of an organic carboxylic acid having 1 to 12 carbon atoms, (2) a salt of said compound with physiologically campatible inorganic or organic acids, and (3) a salt of said compound where $R_9$ is carboxy, with physiologically compatible inorganic or organic bases.

Another object of the present invention is the development of a process for the sedation and relaxing of muscles of warm-blooded animals comprising administering to warm-blooded animals a safe but effective amount of the above cyclobutane derivatives.

A further object is to develop pharmaceutical compositions containing the above cyclobutane derivatives.

These and other objects of the present invention will become more apparent as the description thereof proceeds.

DESCRIPTION OF THE INVENTION

The present invention relates to cyclobutane derivatives having the general formula I; as well as the process of obtaining the cyclobutane derivatives and the process of utilizing the same in pharmaceutical compositions for sedation and muscle relaxation.

Preferred from among the compounds of the general formula I are those trans-cyclobutane compounds where $R_1$, $R_2$ and $R_5$ are hydrogen, $R_3$ is hydroxy, chloro or alkyl having 3 to 5 carbon atoms, $R_4$ is methyl and $R_6$ is phenyl, 4-hydroxyphenyl, 4-methoxyphenyl or pyridyl-2. These preferred compounds have the formula

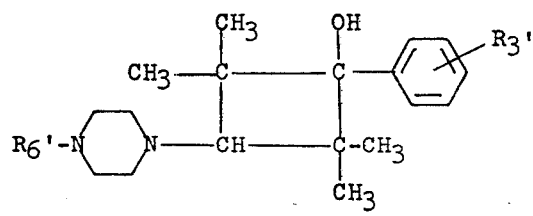

wherein $R_3'$ is selected from the group consisting of hydroxy, chloro and alkyl having 3 to 5 carbon atoms and $R_6'$ is selected from the group consisting of phenyl, 4-hydroxyphenyl, 4-methoxyphenyl and pyridyl-2, as well as the acid addition salts of said compounds with physiologically compatible inorganic or organic acids; where the 1-phenyl is in trans configuration to the cyclobutane ring with respect to the 3-piperazinyl.

The compounds embraced by the above general formula I may be prepared by the following methods.

Method A

For the preparation of compounds of general formula I, wherein none of the radicals $R_1$ to $R_3$ represent an acyloxy group and wherein the radical $R_6$ does not contain an acyloxy or a carbaloxy group:

A compound of general formula II,

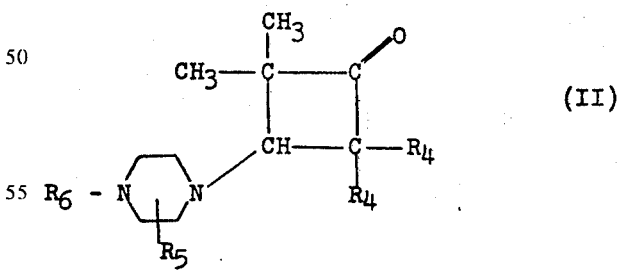

wherein $R_4$, $R_5$ and $R_6$ are defined as above, except that no radicals containing acyloxy and carbalkoxy groups are present, is reacted with a compound of general formula III,

wherein $R_1'$ to $R_3'$ represent hydrogen atoms, halogen atoms, hydroxyl groups protected by a protective group, trifluoromethyl groups, alkyl groups with 1 to 6 carbon atoms, alkoxy groups with 1 to 3 carbon atoms or 2 of the radicals $R_1'$ to $R_3'$ together represents a methylenedioxy group and M represents an alkali metal such as lithium or a magnesium halogenide group.

The reaction is preferably carried out in an anhydrous inert solvent such as ether, tetrahydrofuran or ethylene glycoldimethylether, optionally under a protective gas atmosphere and appropriately at temperatures between −20°C and 100°C, preferably however at the boiling temperature of the solvent used. After the reaction an optionally used protective group for a hydroxy group in a compound of general formula III is split off, for example the benzyl group by means of catalytical hydrogenation or the trimethylsilyl group by means of hydrolysis.

Method B

For general preparation:
A compound of general formula IV,

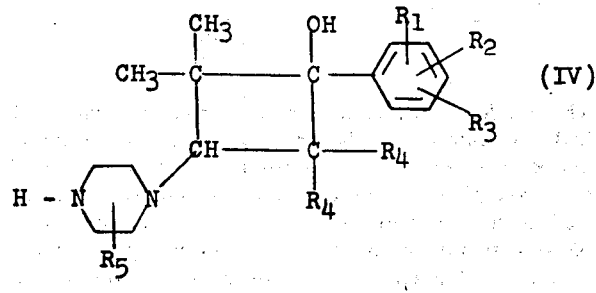

wherein $R_1$ to $R_5$ are defined as above, is reacted with a halogenide of general formula V, $$R_6 - Hal \qquad (V)$$

wherein $R_6$ is defined as above, and Hal represents a chlorine, bromine or iodine atom.

The reaction is appropriately carried out in a solvent such as ethanol, water/ethanol, isopropanol, butanol, dioxane or xylene, optionally in the presence of potassium iodide or in the presence of a catalyst, for example copper powder or anhydrous zinc chloride, and optionally in the presence of an inorganic or organic base, for example an alkali metal carbonate such as sodium carbonate, potassium carbonate or triethylamine, and according to the reactivity of the halogenide used at temperatures between 20°C and 160°C, preferably, however, at 80°C to 130°C.

The reactivity of the halogen atom in a compound of general formula V may be enhanced, if necessary, by the introduction of activating groups, e.g. one or more nitro groups and optionally in addition by the conversion, where $R_6$ is a pyridyl, of the pyridine-nitrogen into the N-oxide, e.g. by means of hydrogen peroxide or a peracid such as perbenzoic acid. After the reaction the compound obtained is converted by means of reduction, e.g. by means of nascent or catalytically activated hydrogen, into the corresponding compound, optionally substituted by one or more amino groups, which on its part may be converted into the desired compound of general formula I using the corresponding diazonium compound.

Furthermore, it may be of advantage, if reactive hydrogen atoms are protected during the reaction by usual protective groups, e.g. by benzyl or trimethylsilyl groups. These protective groups may be split off again after the reaction, e.g. the benzyl group by means of catalytical hydrogenation and the trimethylsilyl group by means of hydrolysis.

Method C

For general preparation:
A compound of general formula VI,

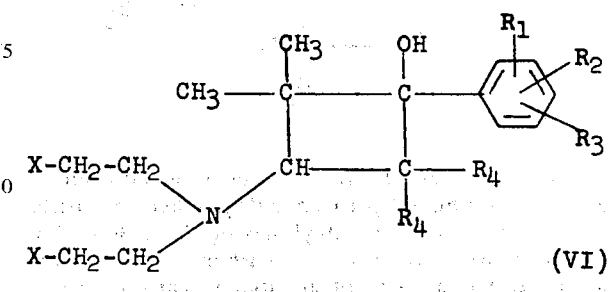

wherein $R_1$, $R_2$, $R_3$ and $R_4$ are defined as above and X represents a halogen atom or the p-toluenesulfonyloxy group, is reacted with an amine of general formula VII, $$R_6 - NH_2 \qquad (VII)$$

wherein $R_6$ is defined as above.

The reaction is optionally carried out in a solvent such as propanol, dioxane or in an excess of the amine used of general formula VII and optionally in the presence of a base such as sodium carbonate, appropriately at temperatures between 50°C and 200°C, preferably however at the boiling temperature of the solvent used.

If according to Methods A, B and C, a compound of general formula I is obtained, which is substituted by one or more halogen atoms, this compound may be dehalogenated by means of usual dehalogenating agents, e.g. by means of catalytical hydrogenation in the presence of palladium-coal and sodium acetate, or if a cis-trans mixture of a compound of general formula I is obtained, this mixture may be separated into the corresponding cis and trans compounds, for example by means of column chromatography and/or if a compound of general formula I is obtained, wherein the radicals $R_1$ to $R_3$ represent acyloxy groups and/or $R_6$ contains an acyloxy and/or carbalkoxy group, these groups may, for example be converted into the free hydroxy groups or respectively the carboxyl group by means of hydrolysis, and/or if a compound of general formula I is obtained, which contains free hydroxy groups, this compound may subsequently be acylated, if desired, with an acylating agent such as a corresponding acid anhydride or halogenide or alkylated with an alkylating agent such as an alkylhalogenide, diazoalkane or dialkylsulfate.

The acylating agent and the acyloxy group are derived from acyls of organic carboxylic acids having 1 to 12 carbon atoms, more particularly alkanoic acids such as acetic acid, isobutyric acid, etc.; and aromatic hydrocarbon carboxylic acids such as benzoic acid. etc.

The obtained compounds of general formula I may be converted into their salts with the corresponding physiologically compatible inorganic or organic acids or, where $R_9$ is carboxyl, bases. As acids for example, inorganic acids such as hydrochloric acid, hydrobromic acid, sulfuric acid and phosphoric acid, and organic acids having 1 to 6 carbon atoms, preferably those containing at least one hydroxyl, such as lactic acid, citric acid, tartaric acid and maleic acid and as bases alkali metal hydroxides, carbonates and ammonium hydroxide, such as sodium hydroxide and potassium hydroxide have proved to be suitable.

A compound of general formula II used as starting material may be prepared by cycloaddition of an enamine of general formula VIII,

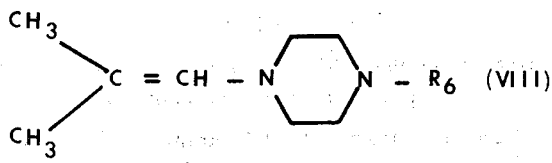

wherein $R_5$ and $R_6$ are defined as above, with a ketene of general formula IX,

wherein $R_4$ is defined as above, in a solvent such as benzene and at temperatures between 20°C and 80°C and by subsequent hydrolysis of an optionally obtained O-acylated compound (see Angew. Chemie 74, 32 (1962); J. Org. Chem. 26, 4775 (1961) and ibid 26, 4776 (1961)).

A compound of general formula VI used as starting material is obtained by addition of ethyleneoxide to an amine of general formula X,

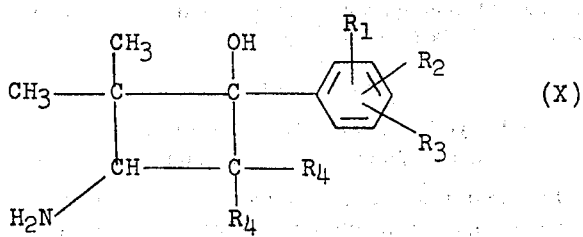

wherein $R_1$ to $R_4$ are defined as above, and subsequent reaction with a halogenating agent such as thionyl chloride.

An amine of general formula X is obtained from the corresponding dibenzyl-compound by hydrogenating removal of the benzyl groups in the presence of palladium/coal. The necessary dibenzyl-compound is obtained by Grignard reaction of a corresponding cyclobutanone-derivate, which may be prepared by cycloaddition from the corresponding enamine with the corresponding ketene.

A compound of general formula IV used as starting material is obtained by reaction of a corresponding substituted cyclobutanone with a corresponding Grignard compound and subsequent removal of the protective group in 4-position of the piperazine, e.g. the benzyl group, in the obtained cyclobutanol-compound for example by means of catalytical hydrogenation.

The following examples illustrate the invention without being limitative.

EXAMPLES

Unless mentioned in the examples, the trans compound has always been that compound isolated, "trans" is utilized in reference to the position of the piperazine ring in comparison to the aromatic nucleus which is in 1-position of the cyclobutane ring.

EXAMPLE 1

1-(4-hydroxyphenyl)-2,2,4,4-tetramethyl-3-[4-(pyridyl-2)-piperazinyl]-cyclobutanol-(1) by method A A solution of 36.8 gm (0.15 mol) of 4-trimethylsilyloxy-bromobenzene in 50 ml of absolute tetrahydrofuran was dropped slowly into 3.64 gm (0.15 mol) of magnesium chips in 30 ml of absolute tetrahydrofuran. After about one-third of the 4-trimethylsilyloxy-bromobenzene had been added, the reaction was set going by warming in the presence of a grain of iodine and was finished while refluxing. At room temperature a solution of 14.4 gm (0.05 mol) of 2,2,4,4-tetramethyl-3-[4-(pyridyl-2)-piperazinyl]-cyclobutanone (m.p. 126°–127°C) in 40 ml of absolute tetrahydrofuran was dropped into the prepared Grignard reagent. In order to complete the reaction the mixture was subsequently refluxed for 3 hours. After standing overnight, 150 ml of 6 N hydrochloric acid were dropped into the reaction mixture while ice-cooling the same. The hydrochloride of the desired product precipitated. The precipitate was filtered off and stirred for 2 hours with an excess of an aqueous sodium hydroxide solution. After vacuum filtering, the precipitate was dissolved in ethyl acetate. Subsequently the ethyl acetate solution was washed with an aqueous sodium hydroxide solution and with water and dried over sodium sulfate. The solvent was removed in vacuo. The crude product was recrystallized once from a little ethanol and once from isopropanol using activated carbon. Yield: 8.2 gm (43% of theory) of colorless crystals. M.P. 214°–216°C.

After addition of an excess of 6 N hydrochloric acid to the hot ethanolic solution of the base the dihydrochloride crystallized out when cooling. M.p. 197°C (decomp.).

The compounds described in the following examples 2–69 were prepared analogously to Example 1.

EXAMPLE 2

1-Phenyl-2,2,4,4-tetramethyl-3-(4-phenylpiperazinyl)-cyclobutanol-(1)

Prepared from 2,2,4,4-tetramethyl-3-(4-phenylpiperazinyl)-cyclobutanone by Grignard reaction with bromobenzene in ether. Yield: 39% of theory; m.p. 113°C (from propanol).

EXAMPLE 3

1-(4-Benzyloxyphenyl)-2,2,4,4-tetramethyl-3-(4-phenylpiperazinyl)-cyclobutanol-(1)

Prepared from 2,2,4,4-tetramethyl-3-(4-phenylpiperazinyl)-cyclobutanone by Grignard reaction with 4-benzyloxy-bromobenzene in tetrahydrofuran. Yield: 16% of theory; m.p. 125°–128°C (from isopropanol).

EXAMPLE 4

1-(3-Benzyloxyphenyl)-2,2,4,4-tetramethyl-3-(4-phenylpiperazinyl)-cyclobutanol-(1)

Prepared from 2,2,4,4-tetramethyl-3-(4-phenylpiperazinyl)-cyclobutanone by Grignard reaction with 3-benzyloxy-bromobenzene in tetrahydrofuran. Yield: 41% of theory; m.p. 108°C (from methanol).

EXAMPLE 5

1-(4-Methoxyphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 4-methoxybromobenzene in tetrahydrofuran. Yield: 54% of theory; m.p. of the trans-compound: 159°–160°C (from ethanol). Yield: 3% of theory; m.p. of the cis-compound: 145°–146°C (from petrolum ether).

EXAMPLE 6

1-(3-Methoxyphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 3-methoxybromobenzene in tetrahydrofuran. Yield: 40% of theory; m.p. of the trans-compound: 168°–169°C (from isopropanol). Yield: 3% of theory; m.p. of the cis-compound: 159°C (from petroleum ether).

EXAMPLE 7

1-(2-Methoxyphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 2-methoxybromobenzene in tetrahydrofuran. Yield: 26% of theory; m.p. 187°–188°C (from ethyl acetate).

EXAMPLE 8

1-(3,4-Dimethoxyphenyl)-2,2,4,4-tetramethyl-3-(4-phenylpiperazinyl)-cyclobutanol-(1)

Prepared from 2,2,4,4-tetramethyl-3-(4-phenyl-piperazinyl)-cyclobutanone by Grignard reaction with 3,4-dimethoxy-bromobenzene in tetrahydrofuran. Yield: 29% of theory; m.p. 188°–190°C (from acetone).

EXAMPLE 9

1-(3,4-Methylenedioxyphenyl)-2,2,4,4-tetramethyl-3-(4-phenylpiperazinyl)-cyclobutanol-(1)

Prepared from 2,2,4,4-tetramethyl-3-(4-phenyl-piperazinyl)-cyclobutanone by Grignard reaction with 3,4-methylene-dioxy-bromobenzene in tetrahydrofuran. Yield: 26% of theory; m.p. 172°–174°C (from ethyl acetate).

EXAMPLE 10

1-(2,3,4-Trimethoxyphenyl)-2,2,4,4-tetramethyl-3-(4-phenylpiperazinyl)-cyclobutanol-(1)

Prepared from 2,2,4,4-tetramethyl-3-(4-phenyl-piperazinyl)-cyclobutanone by Grignard reaction with 2,3,4-trimethoxy-bromobenzene in tetrahydrofuran. Yield: 14% of theory; m.p. of the cis-compound: 148°–150°C (from ethyl acetate).

EXAMPLE 11

1-(4-Methylphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 4-bromotoluene in ether. Yield: 37% of theory; m.p. 84°–87°C (from petroleum ether).

EXAMPLE 12

1-(4-Fluorophenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 4-fluorobromobenzene in ether. Yield: 25% of theory; m.p. 84°–87°C (from petroleum ether).

EXAMPLE 13

1-(4-Bromophenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 1,4-dibromobenzene in ether. Yield: 21% of theory; m.p. 119°–122°C (from ethanol).

EXAMPLE 14

1-(4-Trifluoromethylphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by Grignard reaction with 4-trifluoromethyl-bromobenzene in ether. Yield: 14% of theory; m.p. 113°C (from methanol).

EXAMPLE 15

1-Phenyl-2,2,4,4-tetramethyl-3-[4-(4-methoxyphenyl)-piperazinyl]-cyclobutanol-(1)

Prepared from 2,2,4,4-tetramethyl-3-[4-(4-methoxyphenyl)-piperazinyl]-cyclobutanone by Grignard reaction with bromobenzene in ether. Yield: 19% of theory; m.p. 167°–168°C (from ethanol).

EXAMPLE 16

1-Phenyl-2,2,4,4-tetramethyl-3-[4-(2-methoxyphenyl)-piperazinyl]-cyclobutanol-(1)

Prepared from 2,2,4,4-tetramethyl-3-[4-(2-methoxyphenyl)-piperazinyl]-cyclobutanone by Grignard reaction with bromobenzene in ether. Yield: 41% of theory; m.p. 128°–129°C (from petroleum ether).

EXAMPLE 17

1-Phenyl-2,2,4,4-tetramethyl-3-[4-(4-ethoxyphenyl)-piperazinyl]-cyclobutanol-(1)

Prepared from 2,2,4,4-tetramethyl-3-[4-(4-ethoxyphenyl)-piperazinyl]-cyclobutanone by Grignard reaction with bromobenzene in ether. Yield: 37% of theory; m.p. 154°–155°C (from ethyl acetate).

EXAMPLE 18

1-Phenyl-2,2,4,4-tetramethyl-3-[4-(2-ethoxyphenyl)-piperazinyl]-cyclobutanol-(1)

Prepared from 2,2,4,4-tetramethyl-3-[4-(2-ethoxyphenyl)-piperazinyl]-cyclobutanone by Grignard reaction with bromobenzene in tetrahydrofuran. Yield: 36% of theory; m.p. 90°C, decomposition (from methanol).

EXAMPLE 19

1-Phenyl-2,2,4,4-tetramethyl-3-[4-(2,4-dimethoxyphenyl)-piperazinyl]-cyclobutanol-(1)

Prepared from 2,2,4,4-tetramethyl-3-[4-(2,4-dimethoxyphenyl)-piperazinyl]-cyclobutanone by Grignard reaction with bromobenzene in tetrahydrofuran. Yield: 61% of theory; m.p. 154°–155°C (from methanol).

EXAMPLE 20

1-Phenyl-2,2,4,4-tetramethyl-3-[4-(2-methylphenyl)-piperazinyl]-cyclobutanol-(1)

Prepared from 2,2,4,4-tetramethyl-3-[4-(2-methylphenyl)-piperazinyl]-cyclobutanone by Grignard reaction with bromobenzene in ether. Yield: 17% of theory; m.p. 124°–125°C (from isopropanol).

EXAMPLE 21

1-Phenyl-2,2,4,4-tetramethyl-3-[4-(2,6-dimethylphenyl)-piperazinyl]-cyclobutanol-(1)

Prepared from 2,2,4,4-tetramethyl-3-[4-(2,6-dimethylphenyl)-piperazinyl]-cyclobutanone by Grignard reaction with bromobenzene in ether. Yield: 14% of theory; m.p. 154°–155°C (from ethanol).

EXAMPLE 22

1-Phenyl-2,2,4,4-tetramethyl-3-[4-(2-ethylphenyl)-piperazinyl[-cyclobutanol-(1)

Prepared from 2,2,4,4-tetramethyl-3-[4-(2-ethylphenyl)-piperazinyl]-cyclobutanone by Grignard reaction with bromobenzene in ether. Yield: 38% of theory; m.p. 136°–137°C (from ethanol).

EXAMPLE 23

1-Phenyl-2,2,4,4-tetramethyl-3-[4-(4-fluorophenyl)-piperazinyl]-cyclobutanol-(1)

Prepared from 2,2,4,4-tetramethyl-3-[4-(4-fluorophenyl)-piperazinyl]-cyclobutanone by Grignard reaction with bromobenzene in ether. Yield: 37% of theory; m.p. 165°–166°C (from ethyl acetate).

EXAMPLE 24

1-Phenyl-2,2,4,4-tetramethyl-3-[4-(4-chlorophenyl)-piperazinyl]-cyclobutanol-(1)

Prepared from 2,2,4,4-tetramethyl-3-[4-(4-chlorophenyl)-piperazinyl]-cyclobutanone by Grignard reaction with bromobenzene in ether. Yield: 60% of theory; m.p. 141°–142°C (from isopropanol).

EXAMPLE 25

1-Phenyl-2,2,4,4-tetramethyl-3-[4-(4-bromophenyl)-piperazinyl]-cyclobutanol-(1)

Prepared from 2,2,4,4-tetramethyl-3-[4-(4-bromophenyl)-piperazinyl]-cyclobutanone by Grignard reaction with bromobenzene in ether. Yield: 11% of theory; m.p. 161°C (from petroleum ether).

EXAMPLE 26

1-Phenyl-2,2,4,4-tetramethyl-3-[4-(2-bromophenyl)-piperazinyl]-cyclobutanol-(1)

Prepared from 2,2,4,4-tetramethyl-3-[4-(2-bromophenyl)-piperazinyl]-cyclobutanone by Grignard reaction with bromobenzene in ether. Yield: 14% of theory; m.p. 134°–135°C (from ethanol).

EXAMPLE 27

1-Phenyl-2,2,4,4-tetramethyl-3-[4-(3-trifluoromethylphenyl)-piperazinyl]-cyclobutanol-(1)

Prepared from 2,2,4,4-tetramethyl-3-[4-(3-trifluoromethylphenyl)-piperazinyl]-cyclobutanone by Grignard reaction with bromobenzene in ether. Yield: 30% of theory; m.p. 92°–94°C (from isopropanol).

EXAMPLE 28

1-(4-Hydroxyphenyl)-2,2,4,4-tetramethyl-3-[4-(4-methoxyphenyl)-piperazinyl]-cyclobutanol-(1)

Prepared from 2,2,4,4-tetramethyl-3-[4-(4-methoxyphenyl)-piperazinyl]-cyclobutanone by Grignard reaction with 4-trimethylsilyloxybromobenzene in tetrahydrofuran and subsequent hydrolysis. Yield: 25% of theory; m.p. 200°–201°C (from ethyl acetate/petroleum ether).

EXAMPLE 29

1-(4-Hydroxyphenyl)-2,2,4,4-tetramethyl-3-[4-(2-methoxyphenyl)-piperazinyl]-cyclobutanol-(1)

Prepared from 2,2,4,4-tetramethyl-3-[4-(2-methoxyphenyl)-piperazinyl]-cyclobutanone by Grignard reaction with 4-trimethylsilyloxybromobenzene in tetrahydrofuran and subsequent hydrolysis. Yield: 9% of theory; m.p. 118°–119°C (from carbon tetrachloride).

EXAMPLE 30

1-(4-Hydroxyphenyl)-2,2,4,4-tetramethyl-3-[4-(4-ethoxyphenyl)-piperazinyl]-cyclobutanol-(1)

Prepared from 2,2,4,4-tetramethyl-3-[4-(4-ethoxyphenyl)-piperazinyl]-cyclobutanone by Grignard reaction with 4-trimethylsilyloxybromobenzene in tetrahydrofuran and subsequent hydrolysis. Yield: 6% of theory; m.p. 165°–166°C (from ethyl acetate).

EXAMPLE 31

1-(4-Hydroxyphenyl)-2,2,4,4-tetramethyl-3-[4-(4-benzyloxyphenyl)-piperazinyl]-cyclobutanol-(1)

Prepared from 2,2,4,4-tetramethyl-3-[4-(4-benzyloxyphenyl)-piperazinyl]-cyclobutanone by Grignard reaction with 4-trimethylsilyloxybromobenzene in tetrahydrofuran and subsequent hydrolysis. Yield: 54% of theory; m.p. 194°–195°C (from methanol).

EXAMPLE 32

1-(4-Hydroxyphenyl)-2,2,4,4-tetramethyl-3-[4-(3,4-dimethoxyphenyl)-piperazinyl]-cyclobutanol-(1)

Prepared from 2,2,4,4-tetramethyl-3-[4-(3,4-dimethoxyphenyl)-piperazinyl]-cyclobutanone by Grignard reaction with 4-trimethylsilyloxybromobenzene in tetrahydrofuran and subsequent hydrolysis. Yield: 23% of theory; m.p. 170°–172°C (from chloroform/petroleum ether).

EXAMPLE 33

1-(4-Hydroxyphenyl)-2,2,4,4-tetramethyl-3-[4-(2,4-dimethoxyphenyl)-piperazinyl]-cyclobutanol-(1)

Prepared from 2,2,4,4-tetramethyl-3-[4-(2,4-dimethoxyphenyl)-piperazinyl]-cyclobutanone by Grignard reaction with 4-trimethylsilyloxybromobenzene in tetrahydrofuran and subsequent hydrolysis. Yield: 15% of theory; m.p. 166°–170°C (from methanol).

EXAMPLE 34

1-(4-Hydroxyphenyl)-2,2,4,4-tetramethyl-3-[4-(2-methylphenyl)-piperazinyl]-cyclobutanol-(1)

Prepared from 2,2,4,4-tetramethyl-3-[4-(2-methylphenyl)-piperazinyl]-cyclobutanone by Grignard reaction with 4-trimethylsilyloxybromobenzene in tetrahydrofuran and subsequent hydrolysis. Yield: 20% of theory; m.p. 200°–202°C (from benzene).

EXAMPLE 35

1-(4-Hydroxyphenyl)-2,2,4,4-tetramethyl-3-[4-(2-ethylphenyl)-piperazinyl]-cyclobutanol-(1)

Prepared from 2,2,4,4-tetramethyl-3-[3-(2-ethylphenyl)-piperazinyl]-cyclobutanone by Grignard reaction with 4-trimethylsilyloxybromobenzene in tetrahydrofuran and subsequent hydrolysis. Yield: 57% of theory; m.p. 214°–215°C (from ethanol).

EXAMPLE 36

1-(4-Hydroxyphenyl)-2,2,4,4-tetramethyl-3-[4-(4-fluorophenyl)-piperazinyl]-cyclobutanol-(1)

Prepared from 2,2,4,4-tetramethyl-3-[4-(4-fluorophenyl)-piperazinyl]-cyclobutanone by Grignard reaction with 4-trimethylsilyloxybromobenzene and tetrahydrofuran and subsequent hydrolysis. Yield: 38% of theory; m.p. 192°–193°C (from methanol).

EXAMPLE 37

1-(4-Hydroxyphenyl)-2,2,4,4-tetramethyl-3-[4-(4-bromophenyl)-piperazinyl]-cyclobutanol-(1)

Prepared from 2,2,4,4-tetramethyl-3-[4-(4-bromophenyl)-piperazinyl]-cyclobutanone by Grignard reaction with 4-trimethylsilyloxybromobenzene in tetrahydrofuran and subsequent hydrolysis. Yield: 9% of theory; m.p. 200°–201°C (from methanol).

EXAMPLE 38

1-(4-Hydroxyphenyl)-2,2,4,4-tetramethyl-3-[4-(2-bromophenyl)-piperazinyl]-cyclobutanol-(1)

Prepared from 2,2,4,4-tetramethyl-3-[4-(2-bromophenyl)-piperazinyl]-cyclobutanone by Grignard reaction with 4-trimethylsilyloxybromobenzene in tetrahydrofuran and subsequent hydrolysis. Yield: 34% of theory; m.p. 215°–216°C (from methanol).

EXAMPLE 39

1-(4-Hydroxyphenyl)-2,2,4,4-tetramethyl-3-[4-(3,4-dichlorophenyl)-piperazinyl]-cyclobutanol-(1)

Prepared from 2,2,4,4-tetramethyl-3-[4-(3,4-dichlorophenyl)-piperazinyl]-cyclobutanone by Grignard reaction with 4-trimethylsilyloxybromobenzene in tetrahydrofuran and subsequent hydrolysis. Yield: 15% of theory; m.p. 213°–215°C (from ethyl acetate).

EXAMPLE 40

1-(4-Hydroxyphenyl)-2,2,4,4-tetramethyl-3-[4-(3-trifluoromethylphenyl)-piperazinyl]-cyclobutanol-(1)

Prepared from 2,2,4,4-tetramethyl-3-[4-(3-trifluoromethylphenyl)-piperazinyl]-cyclobutanone by Grignard reaction with 4-trimethylsilyloxybromobenzene in tetrahydrofuran and subsequent hydrolysis. Yield: 25% of theory; m.p. 197°–198°C (from isopropanol).

EXAMPLE 41

1-(4-Hydroxyphenyl)-2,2,4,4-tetramethyl-3-[4-(4-methylmercaptophenyl)-piperazinyl]-cyclobutanol-(1)

Prepared from 2,2,4,4-tetramethyl-3-[4-(4-methylmercaptophenyl)-piperazinyl]-cyclobutanone by Grignard reaction with 4-trimethylsilyloxybromobenzene in tetrahydrofuran and subsequent hydrolysis. Yield: 46% of theory; m.p. 189°–192°C (from isopropanol).

EXAMPLE 42

1-(4-Methoxyphenyl)-2,2,4,4-tetramethyl-3-[4-(4-methoxyphenyl)-piperazinyl]-cyclobutanol-(1)

Prepared from 2,2,4,4-tetramethyl-3-[4-(4-methoxyphenyl)-piperazinyl]-cyclobutanone by Grignard reaction with 4-methoxybromobenzene in tetrahydrofuran. Yield: 61% of theory; m.p. of the trans-compound: 149°–150°C (from ethyl acetate). Yield: 3% of theory; m.p. of the cis-compound: 183°–185°C (from ethanol).

EXAMPLE 43

1-(3,4-Dimethoxyphenyl)-2,2,4,4-tetramethyl-3-[4-(4-methoxyphenyl)-piperazinyl]-cyclobutanol-(1)

Prepared from 2,2,4,4-tetramethyl-3-[4-(4-methoxyphenyl)-piperazinyl]-cyclobutanone by Grignard reaction with 3,4-dimethoxybromobenzene in tetrahydrofuran. Yield: 35% of theory; m.p. 184°–185°C (from ethyl acetate).

EXAMPLE 44

1-(3,4-Dimethoxyphenyl)-2,2,4,4-tetramethyl-3-[4-(2-methoxyphenyl)-piperazinyl]-cyclobutanol-(1)

Prepared from 2,2,4,4-tetramethyl-3-[4-(2-methoxyphenyl)-piperazinyl]-cyclobutanone by Grignard reaction with 3,4-dimethoxybromobenzene in tetrahydrofuran. Yield: 20% of theory; m.p. 151°–153°C (from methanol).

EXAMPLE 45

1-(3,4-Dimethoxyphenyl)-2,2,4,4-tetramethyl-3-[4-(4-fluorophenyl)-piperazinyl]-cyclobutanol-(1)

Prepared from 2,2,4,4-tetramethyl-3-[4-(4-fluorophenyl)-piperazinyl]-cyclobutanone by Grignard reaction with 3,4-dimethoxybromobenzene in tetrahydrofuran. Yield: 18% of theory; m.p. 181°–182°C (from ethyl acetate).

EXAMPLE 46

1-(4-Hydroxyphenyl)-2,2,-dimethyl-3-[4-phenyl-piperazinyl]-cyclobutanol-(1)

Prepared from 2,2-dimethyl-3-[4-phenyl-piperazinyl]-cyclobutanone by Grignard reaction with 4-trimethylsilyloxybromobenzene in tetrahydrofuran and subsequent hydrolysis. Yield: 9% of theory; m.p. of the trans-compound: 198°–200°C (from isopropanol). Yield: 10% of theory; m.p. of the ciscompound: 151°–153°C (from ethyl acetate).

EXAMPLE 47

1-(4-Hydroxyphenyl)-2,2,4,4-tetramethyl-3-[3-methyl-4-phenylpiperazinyl]-cyclobutanol-(1)

Prepared from 2,2,4,4-tetramethyl-3-[3-methyl-4-phenyl-piperazinyl]-cyclobutanone by Grignard reaction with 4-trimethylsilyloxybromobenzene in tetrahydrofuran and subsequent hydrolysis. Yield: 52% of theory; m.p. 153°–154°C (from ethanol).

EXAMPLE 48

1-Phenyl-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with bromobenzene in ether. Yield: 19% of theory; m.p. 135°–136°C (from benzene).

EXAMPLE 49

1-(4-Methoxyphenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 4-methoxybromobenzene in tetrahydrofuran. Yield: 19% of theory; m.p. of the dihydrochloride: 138°–140°C (decomp.).

EXAMPLE 50

1-(3,4-Dimethoxyphenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 3,4-dimethoxybromobenzene in tetrahydrofuran. Yield: 30% of theory; m.p. 201°–203°C (from chloroform/ether).

EXAMPLE 51

1-(2,3,4-Trimethoxyphenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 2,3,4-trimethoxybromobenzene in tetrahydrofuran. Yield: 23% of theory; m.p. of the cis/trans-mixture: 135°–136°C (from ethanol).

EXAMPLE 52

1-(4-Methylphenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 4-bromotoluene in ether. Yield: 23% of theory; m.p. 140°–142°C (from ethanol).

EXAMPLE 53

1-(4-Fluorophenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 4-fluorobromobenzene in ether. Yield: 31% of theory; m.p. 150°–152°C (from methanol).

EXAMPLE 54

1-(4-Bromophenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 1,4-dibromobenzene in ether. Yield: 20% of theory; m.p. of the dihydrochloride: 242°–244°C (decomp.).

EXAMPLE 55

1-(4-Trifluoromethylphenyl)-2,2,4,4-tetramethyl-3-[4-pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 4-trifluoromethylbromobenzene in ether. Yield: 21% of theory; m.p. 123°–124°C (from petroleum ether).

EXAMPLE 56

1-Phenyl-2,2,4,4-tetramethyl-3-[4-(3-methyl-pyridyl-2)-piperazinyl]-cyclobutanol-(1)

Prepared from 2,2,4,4-tetramethyl-3-[4-(3-methyl-pyridyl-2)-piperazinyl]-cyclobutanone by Grignard reaction with bromobenzene in ether. Yield: 39% of theory; m.p. 175°–177°C (from acetone).

EXAMPLE 57

1-(4-Hydroxyphenyl)-2,2,4,4-tetramethyl-3-[4-(3-methylpyridyl-2)-piperazinyl]-cyclobutanol-(1)

Prepared from 2,2,4,4-tetramethyl-3-[4-(3-methyl-pyridyl-2)-piperazinyl]-cyclobutanone by Grignard reaction with 4-trimethylsilyloxybromobenzene in tetrahydrofuran and subsequent hydrolysis. Yield: 45% of theory; m.p. of the dihydrochloride: 162°C.

EXAMPLE 58

1-Phenyl-2,2,4,4-tetramethyl-3-[4-(4-methyl-pyridyl-2)-piperazinyl]-cyclobutanol-(1)

Prepared from 2,2,4,4-tetramethyl-3-[4-(4-methyl-pyridyl-2)-piperazinyl]-cyclobutanone by Grignard reaction with bromobenzene in ether. Yield: 14% of theory; m.p. 124°–126°C, decomposition (from ethyl acetate).

EXAMPLE 59

1-(4-Hydroxyphenyl)-2,2,4,4-tetramethyl-3-[4-(4-methyl-pyridyl-2)-piperazinyl]-cyclobutanol-(1)

Prepared from 2,2,4,4-tetramethyl-3-[4-(4-methyl-pyridyl-2)-piperazinyl]-cyclobutanone by Grignard reaction with 4-trimethylsilyloxybromobenzene in tetrahydrofuran and subsequent hydrolysis. Yield: 32% of theory; m.p. 202°–203°C (from ethyl acetate).

EXAMPLE 60

1-Phenyl-2,2,4,4-tetramethyl-3-[4-(6-methyl-pyridyl-2)-piperazinyl]-cyclobutanol-(1)

Prepared from 2,2,4,4-tetramethyl-3-[4-(6-methyl-pyridyl-2)-piperazinyl]-cyclobutanone by Grignard reaction with bromobenzene in tetrahydrofuran. Yield: 57% of theory. m.p. 126°–128°C (from isopropanol).

EXAMPLE 61

1-(4-Hydroxyphenyl)-2,2,4,4-tetramethyl-3-[4-(6-methyl-pyridyl-2)-piperazinyl]-cyclobutanol-(1)

Prepared from 2,2,4,4-tetramethyl-3-[4-(6-methyl-pyridyl-2)-piperazinyl]-cyclobutanone by Grignard reaction with 4-trimethylsilyloxybromobenzene in tetrahydrofuran and subsequent hydrolysis. Yield: 61% of theory; m.p. 201°C (from acetone).

EXAMPLE 62

1-Phenyl-2,2,4,4-tetramethyl-3-[4-(5-bromo-pyridyl-2)-piperazinyl]-cyclobutanol-(1)

Prepared from 2,2,4,4-tetramethyl-3-[4-(5-bromopyridyl-2)-piperazinyl]-cyclobutanone by Grignard reaction with bromobenzene in ether. Yield: 35% of theory; m.p. 159°–160°C (from ethyl acetate).

EXAMPLE 63

1-(4-Hydroxyphenyl)-2,2,4,4-tetramethyl-3-[4-(5-bromo-pyridyl-2)-piperazinyl]-cyclobutanol-(1)

Prepared from 2,2,4,4-tetramethyl-3-[4-(5-bromopyridyl-2)-piperazinyl]-cyclobutanone by Grignard reaction with 4-trimethylsilyloxybromobenzene in tetrahydrofuran and subsequent hydrolysis. Yield: 4% of theory; m.p. 193°C, decomposition (from ethyl acetate).

EXAMPLE 64

1-Phenyl-2,2-dimethyl-3-[4-(pyridyl-2)-piperazinyl]-cyclobutanol-(1)

Prepared from 2,2-dimethyl-3-[4-(pyridyl-2)-piperazinyl]-cyclobutanone by Grignard reaction with bromobenzene in ether. Yield: 19% of theory; m.p. 181°–183°C (from chloroform/methanol).

EXAMPLE 65

1-(4-Hydroxyphenyl)-2,2-dimethyl-3-[4-(pyridyl-2)-piperazinly]-cyclobutanol-(1)

Prepared from 2,2-dimethyl-3-[4-(pyridyl-2)-piperazinyl]-cyclobutanone by Grignard reaction with 4-trimethylsilyloxybromobenzene in tetrahydrofuran and subsequent hydrolysis. Yield: 21% of theory; m.p. 186°–187°C (from ethanol).

EXAMPLE 66

1-Phenyl-2,2,4,4-tetramethyl-3-[2-methyl-4-(pyridyl-2)-piperazinyl]-cyclobutanol-(1)

Prepared from 2,2,4,4-tetramethyl-3-[2-methyl-4-(pyridyl-2)-piperazinyl]-cyclobutanone by Grignard reaction with bromobenzene in ether. Yield: 11% of theory; m.p. 158°–159°C (from ethanol).

EXAMPLE 67

1-(4-Hydroxyphenyl)-2,2,4,4-tetramethyl-3-[2-methyl-4-(pryidyl-2)-piperazinyl]-cyclobutanol-(1)

Prepared from 2,2,4,4-tetramethyl-3-[2-methyl-4-(pyridyl-2)-piperazinyl]-cyclobutanone by Grignard reaction with 4-trimethylsilyloxybromobenzene in tetrahydrofuran and subsequent hydrolysis. Yield: 11% of theory; m.p. 181°–183°C (from ethyl acetate).

EXAMPLE 68

1-(4-Isopropoxyphenyl)-2,2,4,4-tetramethyl-3-[4-phenylpiperazinyl]-cyclobutanol-(1)

Prepared from 2,2,4,4-tetramethyl-3-(4-phenyl-piperazinyl)-cyclobutanone by Grignard reaction with 4-isopropoxybromobenzene in tetrahydrofuran. Yield: 42% of theory; m.p. 131°–132°C (from methanol).

EXAMPLE 69

1-(4-Isopropoxyphenyl)-2,2,4,4-tetramethyl-3-[4-(pyridyl-2)-piperazinyl]-cyclobutanol-(1)

Prepared from 2,2,4,4-tetramethyl-3-[4-(pyridyl-2)-piperazinyl]-cyclobutanone by Grignard reaction with 4-isopropoxybromobenzene in tetrahydrofuran. Yield: 62% of theory; m.p. 107°–108°C (from isopropanol).

EXAMPLE 70

1-Phenyl-2,2-dimethyl-4,4-diethyl-3-[4-phenyl-piperazinyl]-cyclobutanol-(1) by method A 3.0 gm of bromobenzene were added to 0.84 gm (0.12 mol) of finely cut lithium in 50 ml of absolute ether. This mixture was warmed until the reaction started, then another 6.5 gm of bromobenzene in 50 ml of absolute ether were dropped into it (total 9.5 gm = 0.06 mol of bromobenzene). The reaction mixture was warmed up to its boiling point for 3 hours. At room temperature, a solution of 6.3 gm (0.02 mol) of 2,2-dimethyl-4,4-diethyl-3-[4-phenyl-piperazinyl]-cyclobutanone (m.p. 67°–69°C) in 50 ml of absolute ether was dropped into the reaction mixture which was subsequently refluxed for 5 hours, then mixed with 50 ml of 6 N hydrochloric acid and 200 ml of water while ice-cooling. The layers were separated in a separatory funnel. The aqueous phase was made alkaline with diluted sodium hydroxide solution and extracted three times with ethyl acetate. After drying over sodium sulfate, the ethyl acetate solution was evaporated in vacuo. The residue was recrystallized twice from petroleum ether. 3.5 gm (44% of theory) of a cis-trans-mixture of 1-phenyl-2,2-dimethyl-4,4-diethyl-3-(4-phenyl-piperazinyl)-cyclobutanol-(1) were obtained. M.p. 100°–102°C.

EXAMPLE 71

1-(2,4,6-trimethylphenyl)-2,2,4,4-tetramethyl-3-(4-phenyl-piperazinyl)-cyclobutanol-(1)

Prepared from 2,2,4,4-tetramethyl-3-(4-phenyl-piperazinyl)-cyclobutanone by reaction with 2,4,6-trimethylbromobenzene and lithium analogous to Example 70. Yield: 30% of theory; m.p. 152°–153°C (from isopropanol).

EXAMPLE 72

1-Phenyl-2,2,4,4-tetramethyl-3-[4-(4-hydroxyphenyl)-piperazinyl]-cyclobutanol-(1)

6.0 gm (0.013 mol) of 1-phenyl-2,2,4,4-tetramethyl-3-[4-benzyloxyphenyl)-piperazinyl]-cyclobutanol-(1) were hydrogenated within 4 hours in 80 ml of glacial acetic acid over 1 gm of 10% palladium on carbon at 50°C and a pressure of 50 atmospheres. The catalyst was filtered off, the filtrate evaporated in vacuo and the residue poured into a diluted sodium hydroxide solution and extracted with ethyl acetate. The crude product obtained from the ethyl acetate solution was recrystallized twice from ethanol thus furnishing 2.7 gm (54% of theory) of colorless crystals with m.p. 191°–193°C.

EXAMPLE 73

1-(4-Hydroxyphenyl)-2,2,4,4-tetramethyl-3-[4-hydroxyphenyl)-piperazinyl]-cyclobutanol-(1)

Prepared analogously to Example 72 by hydrogenation of 1-(4-hydroxyphenyl)-2,2,4,4-tetramethyl-3-[4-(4-benzyloxyphenyl)-piperazinyl]-cyclobutanol-(1) in glacial acetic acid over palladium on carbon at 50°C. Yield: 33% of theory; m.p. 217°–220°C (from methanol).

EXAMPLE 74

1-(4-Hydroxyphenyl)-2,2,4,4-tetramethyl-3-[4-phenyl-piperazinyl]-cyclobutanol-(1)

Prepared analogously to Example 72 by hydrogenation of 1-(4-benzyloxyphenyl)-2,2,4,4-tetramethyl-3-[4-phenyl-piperazinyl]-cyclobutanol-(1) in ethanol over palladium on carbon at room temperature. Purification by means of column chromatography. Yield: 57% of theory; m.p. 198°–200°C (from benzene).

EXAMPLE 75

1-(3-Hydroxyphenyl)-2,2,4,4-tetramethyl-3-[4-phenyl-piperazinyl]-cyclobutanol-(1)

Prepared analogously to Example 72 by hydrogenation of 1-(3-benzyloxyphenyl)-2,2,4,4-tetramethyl-3-[4-phenyl-piperazinyl]-cyclobutanol-(1) in ethanol over palladium on carbon at 50°C. Purification by means of column chromatography. Yield: 39% of theory; m.p. 210°–211°C (from methanol).

EXAMPLE 76

1-(4-Acetoxyphenyl)-2,2,4,4-tetramethyl-3-[4-phenyl-piperazinyl]-cyclobutanol-(1)

A solution of 6.5 gm (0.064 mol) of acetic acid anhydride in 50 ml of pyridine was dropped while stirring at 0°C into 6.0 gm (0.016 mol) of 1-(4-hydroxyphenyl)-2,2,4,4-tetramethyl-3-[4-phenyl-piperazinyl]-cyclobutanol-(1) in 50 ml of pyridine. The reaction mixture was left standing overnight at 5°C, then it was poured into ice water and extracted with chloroform. The chloroform layer was washed with water, dried over sodium sulfate and evaporated in vacuo. After recrystallizing the residue twice from ethyl acetate 4.5 gm (68% of theory) of the desired end product were obtained. M.p. 196°–199°C.

EXAMPLE 77

1-Phenyl-2,2,4,4-tetramethyl-3-[4-(4-acetoxyphenyl)-piperazinyl]-cyclobutanol-(1)

Prepared analogously to Example 76 by acetylation of 1-phenyl-2,2,4,4-tetramethyl-3-[4-(4-hydroxyphenyl)-piperazinyl]-cyclobutanol-(1) with acetic acid anhydride in pyridine. Yield: 72% of theory; m.p. 143°–145°C (from methanol).

EXAMPLE 78

1-(4-Benzoyloxyphenyl)-2,2,4,4-tetramethyl-3-[4-(4-fluorophenyl)-piperazinyl]-cyclobutanol-(1)

A mixture of 3.5 gm (0.009 mol) of 1-(4-hydroxyphenyl)-2,2,4,4-tetramethyl-3-[4-(4-fluorophenyl)-piperazinyl]-cyclobutanol-(1), 2.8 gm (0.020 mol) of benzoylchloride, 2.8 gm (0.020 mol) of potassium carbonate and 40 ml of absolute dioxane was heated for 4 hours up to 100°C. After cooling the precipitate was filtered off, the filtrate evaporated in vacuo and the residue recrystallized from methanol and ethanol. Yield: 1.9 gm (42% of theory), m.p. 185°–187°C.

EXAMPLE 79

1-(4-Benzoyloxyphenyl)-2,2,4,4-tetramethyl-3-[4-(pyridyl-2)-piperazinyl]-cyclobutanol-(1)

Prepared analogously to Example 78 by reaction of 1-(4-hydroxyphenyl)-2,2,4,4-tetramethyl-3-[4-(pyridyl-2)-piperazinyl]-cyclobutanol-(1) with benzoylchloride in the presence of potassium carbonate in boiling dioxane. Yield: 51% of theory; m.p. 180°–182°C (from ethyl acetate).

EXAMPLE 80

1-(4-Isobutyryloxyphenyl)-2,2,4,4-tetramethyl-3-[4-(2-ethylphenyl)-piperazinyl]-cyclobutanol-(1)

Prepared analogously to Example 78 by reaction of 1-(4-hydroxyphenyl)-2,2,4,4-tetramethyl-3-[4-(2-ethylphenyl)-piperazinyl]-cyclobutanol-(1) with isobutyrylchloride in the presence of potassium carbonate in boiling acetone. Yield: 50% of theory; m.p. 130°–133°C (from methanol).

EXAMPLE 81

1-(4-Isobutyryloxyphenyl)-2,2,4,4-tetramethyl-3-[4-(pyridyl-2)-piperazinyl]-cyclobutanol-(1)

Prepared analogously to Example 78 by reaction of 1-(4-hydroxyphenyl)-2,2,4,4-tetramethyl-3-[4-(pyridyl-2)-piperazinyl]-cyclobutanol-(1) with isobutyrylchloride in the presence of potassium carbonate in boiling acetone. Yield: 54% of theory; m.p. 133°–135°C (from acetone).

EXAMPLE 82

1-Phenyl-2,2,4,4-tetramethyl-3-[4-(4-benzoyloxyphenyl)-piperazinyl]-cyclobutanol-(1)

Prepared analogously to Example 78 by reaction of 1-phenyl-2,2,4,4-tetramethyl-3-[4-(4-hydroxyphenyl)-piperazinyl]-cyclobutanol-(1) with benzoylchloride in the presence of potassium carbonate in boiling dioxane. Yield: 8% of theory; m.p. 197°–198°C (from methanol).

EXAMPLE 83

1-Phenyl-2,2,4,4-tetramethyl-3-[4-(4-isobutyryloxyphenyl)-piperazinyl]-cyclobutanol-(1)

Prepared analogously to Example 78 by reaction of 1-phenyl-2,2,4,4-tetramethyl-3-[4-(4-hydroxyphenyl)-piperazinyl]-cyclobutanol-(1) with isobutyrylchloride in the presence of triethylamine in ether at 20°C. Yield: 47% of theory; m.p. 148°–149°C (from petroleum ether).

EXAMPLE 84

1-Phenyl-2,2,4,4-tetramethyl-3-[4-(3-acetoxy-pyridyl-2)-piperazinyl]-cyclobutanol-(1)

Prepared analogously to Example 76 by acetylation of 1-phenyl-2,2,4,4-tetramethyl-3-[4-(3-hydroxy-pyridyl-2)-piperazinyl]-cyclobutanol-(1) with acetic acid anhydride in pyridine. Yield: 47% of theory; m.p. 165°–166°C (from ethanol).

EXAMPLE 85

1-(4-Hydroxyphenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-trimethylsilyloxybromobenzene in tetrahydrofuran and subsequent hydrolysis. The cis-compound was separated from the trans-compound which had been produced predominantly by means of column chromatography with benzene/acetone = 85:15. Yield: 2% of theory; m.p. of the cis-compound: 203°–205°C (from isopropanol).

EXAMPLE 86

1-Phenyl-2,2,4,4-tetramethyl-3-[4-(3-benzyloxy-pyridyl-2)-piperazinyl]-cyclobutanol-(1)

Prepared analogously to Example 1 from 2,2,4,4-tetramethyl-3-[4-(3-benzyloxy-pyridyl-2)-piperazinyl]-cyclobutanone by Grignard reaction with bromobenzene in ether. Yield: 53% of theory; m.p. of the dihydrochloride; 163°–168°C.

EXAMPLE 87

1-(4-Hydroxyphenyl)-2,2,4,4-tetramethyl-3-[4-(3-benzyloxy-pyridyl-2)-piperazinyl]-cyclobutanol-(1)

Prepared analogously to Example 1 from 2,2,4,4-tetramethyl-3-[4-(3-benzyloxy-pyridyl-2)-piperazinyl]-cyclobutanone by Grignard reaction with 4-trimethylsilyloxybromobenzene in tetrahydrofuran and subsequent hydrolysis. Yield: 26% of theory; m.p. 195°–196°C (from isopropanol).

EXAMPLE 88

1-(4-Isopropylphenyl)-2,2,4,4-tetramethyl-3-(4-phenyl-piperazinyl)-cyclobutanol-(1)

Prepared analogously to Example 1 from 2,2,4,4-tetramethyl-3-(4-phenyl-piperazinyl)-cyclobutanone by Grignard reaction with 4-isopropylbromobenzene in tetrahydrofuran. Yield: 16% of theory; m.p. 121°–123°C (from ethyl acetate).

EXAMPLE 89

1-(4-Isopropylphenyl)-2,2,4,4-tetramethyl-3-[4-(pyridyl-2)-piperazinyl]-cyclobutanol-(1)

Prepared analogous to Example 1 from 2,2,4,4-tetramethyl-3-[4-(pyridyl-2)-piperazinyl]-cyclobutanone by Grignard reaction with 4-isopropylbromobenzene in tetrahydrofuran. Yield: 20% of theory; m.p. 118°–120°C (from petroleum ether).

EXAMPLE 90

1-(4-Chlorophenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-chlorobromobenzene in ether. Yield: 25% of theory; m.p. 151°–152°C (from ethanol).

EXAMPLE 91

1-Phenyl-2,2,4,4-tetramethyl-3-[4-(3-hydroxy-pyridyl-2)-piperazinyl]-cyclobutanol-(1)

Prepared analogously to Example 72 by hydrogenation of 1-phenyl-2,2,4,4-tetramethyl-3-[4-(3-benzyloxy-pyridyl-2)-piperazinyl]-cyclobutanol-(1) in methanol/water (9:1) over palladium on carbon at room temperature. Purification by means of column chromatography. Yield: 43% of theory; m.p. 196°–197°C.

EXAMPLE 92

1-(4-Hydroxy-phenyl)-2,2,4,4-tetramethyl-3-[4-(3-hydroxy-pyridyl-2)-piperazinyl]-cyclobutanol-(1)

Prepared analogously to Example 72 by hydrogenation of 1-(4-hydroxyphenyl)-2,2,4,4-tetramethyl-3-[4-(3-benzyloxy-pyridyl-2)-piperazinyl]-cyclobutanol-(1) in methanol/water (9:1) over palladium on carbon at room temperature. Purification by means of column chromatography. Yield: 43% of theory; m.p. 218°–220°C.

EXAMPLE 93

1-Phenyl-2,2,4,4-tetramethyl-3-[4-(4-isopropoxy-phenyl)-piperazinyl]-cyclobutanol-(1)

A mixture consisting of 1.0 gm (2.6 millimols) of 1-phenyl-2,2,4,4-tetramethyl-3-[4-(4-hydroxyphenyl)-piperazinyl]-cyclobutanol-(1), 0.4 gm (3.0 millimols) of isopropylbromide, 0.4 gm (2.6 millimols) of potassium carbonate and 100 ml of ethanol was heated for 16 hours to its boiling point while stirring. The precipitate was filtered off, the filtrate evaporated in vacuo and the residue mixed with ether and extracted three times with 2 N sodium hydroxide solution and once with water. The organic phase was dried and evaporated, thus isolating the crude product. After recrystallization from methanol 0.6 gm (55% of theory) of colorless crystals were obtained. M.p. 105°–106°C.

EXAMPLE 94

1-(4-Ethoxyphenyl)-2,2,4,4-tetramethyl-3-[4-(pyridyl-2)-piperazinyl]-cyclobutanol-(1)

At 5°C, 0.4 gm (2.6 millimols) of diethylsulfate were added slowly to 1.0 gm (2.6 millimols) of 1-(4-hydroxy-phenyl)-2,2,4,4-tetramethyl-3-[4-(pyridyl-2)-piperazinyl]-cyclobutanol-(1) in 1.5 ml of 10% sodium hydroxide solution. The reaction mixture was stirred for one hour at room temperature, then heated for three hours up to 80°C and extracted twice with benzene. The benzene layer was washed with diluted sodium hydroxide solution and dried over sodium sulfate. The solvent was removed in vacuo, the residue crystallized wheen triturated with petroleum ehter. Yield: 0.1 gm (9% of theory); m.p. 114°–115°C.

EXAMPLE 95

1-Phenyl-2,2,4,4-tetramethyl-3-[4-(3-methoxy-pyridyl-2)-piperazinyl]-cyclobutanol-(1)

To a solution of 1.1 gm (0.026 mol) of diazomethane in 60 ml of ether (prepared from nitrosomethyl carbamide and potassium hydroxide) were added, at 0°C, 1.5 gm (0.004 mol) of 1-phenyl-2,2,4,4-tetramethyl-3-[4-(3-hydroxy-pyridyl-2)-piperazinyl]-cyclobutanol-(1) dissolved in 25 ml of ethanol. The mixture was warmed to room temperature and stirred for two hours. The excessive diazomethane was destroyed by addition of glacial acetic acid. The reaction mixture was evaporated in vacuo, the residue dissolved in 2N hydrochloric acid and extracted with ether. The aqueous phase was made alkaline with diluted sodium hydroxide solution and extracted with ether (three times). After evaporation the crude product was dissolved in ethyl acetate and converted into its dihydrochloride by addition of etheric hydrochloric acid. When filtered off 1.2 gm (65% of theory) of crystals of the dihydrochloride were obtained. M.p. 238°C (decmop.).

EXAMPLE 96

1-Phenyl-2,2,4,4-tetramethyl-3-[4-(3-carbethoxy-pyridyl-2)-piperazinyl]-cyclobutanol-(1) by method B 1.0 gm (3.5 millimols) of 1-phenyl-2,2,4,4-tetramethyl-3-piperazinyl-cyclobutanol-(1) (m.p. 172°–174°C) and 0.8 gm (3.5 milliomls) of 2-bromopyridine-3-carboxylic acidethyl ester were heated up to 100°C in 10 ml of absolute xylene for 17 hours. 30 ml of ethyl acetate were added to the reaction mixture which was then washed three times with diluted soda solution. The organic layer was separated in a separatory funnel, dried over sodium sulfate and evaporated in vacuo. From the residue the desired end product was isolated by means of column chromatography over silica gel with benzene/acetone = 9:1 and recrystallized from acetone, yielding 0.6 gm (40% of theory) of colorless crystals. M.p. 171°–172°C.

EXAMPLE 97

1-Phenyl-2,2,4,4-tetramethyl-3-[4-(3-carbomethoxy-pyridyl-2)-piperazinyl]-cyclobutanol-(1)

Prepared analogously to Example 96 by reaction of 1-phenyl-2,2,4,4-tetramethyl-3-piperazinyl-cyclobutanol-(1) with 2-bromopyridine-3-carboxylic acid methyl ester in the presence of potassium carbonate in xylene at 100°C. Yield: 18% of theory; m.p. 181°-182°C (from methanol).

EXAMPLE 98

1(4-Hydroxyphenyl)-2,2,4,4-tetramethyl-3-[4-(3-carboethoxypyridyl-2)-piperazinyl]-cyclobutanol-(1)

Prepared analogously to Example 96 by reaction of 1-(4-hydroxyphenyl)-2,2,4,4-tetramethyl-3-piperazinyl-cyclobutanol-(1) (m.p. of the crude product: 208°–209°C, decomp.) with 2-bromopyridine-3-carboxylic acid ethyl ester in the presence of triethylamine in boiling ethanol (99%). Isolation by means of column chromatography over silica gel. Yield: 25% of theory; m.p. 162°–163°C (from ether/petroleum ether).

EXAMPLE 99

1-(4-Hydroxyphenyl)-2,2,4,4-tetramethyl-3-[4-(3-carbomethoxy pyridyl-2)-piperazinyl]-cyclobutanol-(1)

Prepared analogously to Example 96 by reaction of 1-(4-hydroxyphenyl)-2,2,4,4-tetramethyl-3-piperazinyl-cyclobutanol-(1) with 2-bromo-pyridine-3-carboxylic acid-methyl ester in the presence of potassium carbonate in xylene at 100°C. Yield: 13% of theory; m.p. 165°–166°C (from benzene).

EXAMPLE 100

1-Phenyl-2,2,4,4-tetramethyl-3-[4-(3-carboxy-pyridyl-2)-piperazinyl]-cyclobutanol-(1)

Prepared analogously to Example 96 by reaction of 1-phenyl-2,2,4,4-tetramethyl-3-piperazinyl-cyclobutanol-(1) with 2-bromopyridine-3-carboxylic acid in the presence of potassium iodide and copper power in xylene at 120°C. Yield: 22% of theory; m.p. 210°C (decomp.).

EXAMPLE 101

1-Phenyl-2,2,4,4-tetramethyl-3-[4-(pyridyl-2)-piperazinyl]-cyclobutanol-(1)

Prepared analogously to Example 96 by reaction of 1-phenyl-2,2,4,4-tetramethyl-3-piperazinyl-cyclobutanol-(1) with 2-iodopyridine in the presence of water-free zinc-chloride in xylene at 130°C. Purified by means of column chromatography over silica gel. Yield: 12% of theory; m.p. 134°–136°C.

EXAMPLE 102

1-Phenyl-2,2,4,4-tetramethyl-3-[4-(3-carboxy-pyridyl-2)-piperazinyl]-cyclobutanol-(1)

A mixture consisting of 440 mgm (1 millimol) of 1-phenyl-2,2,4,4-tetramethyl-3-[4-(3-carboethoxy-pyridyl-2)-piperazinyl]-cyclobutanol-(1), 5 ml of 1 N sodium hydroxide solution (5 millimols of sodium hydroxide solution) and 10 ml of ethanol was heated for 20 minutes up to 100°C. After cooling, about 0.4 ml of glacial acetic acid were added until the reaction mixture reached a pH-value of 5–6. Subsequently it was evaporated in vacuo to a volume of about 5 ml. The precipitated product was filtered off yielding 250 mgm (61% of theory) of colorless crystals. M.p. 210°C (decomp.).

EXAMPLE 103

1-(4-Ethylphenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-ethyl-bromobenzene in tetrahydrofuran. Yield: 31% of theory; m.p. 122°–123°C (from isopropanol).

EXAMPLE 104

1-(4-Propylphenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-propyl-bromobenzene in tetrahydrofuran. Yield: 38% of theory; m.p. 123°–124°C (from isopropanol).

EXAMPLE 105

1-(4-Butyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-butyl-bromobenzene in tetrahydrofuran. Yield: 51% of theory; m.p. 112°–113°C (from isopropanol).

EXAMPLE 106

D,L-1-(4-butyl-(2)-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4 butyl-(2)-bromobenzene in tetrahydrofuran. Yield: 38% of theory; m.p. 91°–93°C (from petroleum ether).

EXAMPLE 107

1(4-Isobutyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-isobutyl-bromobenzene in tetrahydrofuran. Yield: 58% of theory; m.p. 140°–141°C (from isopropanol).

EXAMPLE 108

1-(4-tert.butyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-tert.butyl-bromobenzene in tetrahydrofuran. Yield: 26% of theory; m.p. 176°C (from methanol).

EXAMPLE 109

1-(4-n-pentyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-n-pentyl-bromobenzene in tetrahydrofuran. Yield: 50% of theory; m.p. 90°–92°C (from petroleum ether).

EXAMPLE 110

1-(4-tert.pentyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-tert.pentyl-bromobenzene in tetrahydrofuran. Yield: 63% of theory; m.p. 152°–153°C (from petroleum ether).

EXAMPLE 111

1-(4-Cyclohexyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 4-cyclohexyl-bromobenzene in tetrahydrofuran. Yield: 54% of theory; m.p. 154°C (from ethanol).

EXAMPLE 112

1-(3-Hydroxy-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 3-trimethylsilyloxy-bromobenzene in tetrahydrofuran and subsequent splitting off of the trimethylsilyl protective group with dilute hydrochloric acid. Yield: 23% of theory; m.p. 211°–212°C (from ethyl acetate).

EXAMPLE 113

1-(2-Hydroxy-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with a mixture consisting of 2-trimethylsilyloxy-bromobenzene and 4-trimethylsilyloxy-bromobenzene (ratio = 1:1) in tetrahydrofuran and subsequent splitting off of the trimethylsilyl protective group with dilute hydrochloric acid. Separation by means of column chromatography over silica gel, eluant: chloroform/acetone = 4:1. Yield: 1.3% of theory; m.p. 142°C.

EXAMPLE 114

1-(3-Chloro-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 3-chloro-bromobenzene in ether. Yield: 31% of theory; m.p. 198°–199°C (from ethanol).

EXAMPLE 115

1-(2-Chloro-phenyl)-2,2,4,4-tetramethyl-3-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 2-chloro-bromobenzene in ether. Yield: 30% of theory; m.p. 91°C (from ethanol).

EXAMPLE 116

1-(3-Methyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 3-methyl-bromobenzene in tetrahydrofuran. Yield: 34% of theory; m.p. 151°C (from isopropanol).

EXAMPLE 117

1-(2-Methyl-phenyl)-2,2,4,4-tetramethyl-3-[4-(pyridyl-2)-piperazinyl]-cyclobutanol-(1)

Prepared analogously to Example 1 from 2,2,4,4-tetramethyl-3-[4-(pyridyl-2)-piperazinyl]-cyclobutanone by Grignard reaction with 2-methyl-bromobenzene in tetrahydrofuran. Yield: 46% of theory; m.p. 137°–138°C (from isopropanol).

EXAMPLE 118

1-(Hydroxy-phenyl)-2,2,4,4-tetramethyl-3-[4-(pyridyl-3)-piperazinyl]-cyclobutanol-(1)

Prepared analogously to Example 1 from 2,2,4,4-tetramethyl-3-[4-(pyridyl-3)-piperazinyl]-cyclobutanone by Grignard reaction with 4-trimethylsilyloxybromobenzene in tetrahydrofuran and subsequent splitting off of the protective group by hydrolysis with dilute hydrochloric acid. Yield: 34% of theory; m.p. 231°–233°C (from ethanol).

EXAMPLE 119

1-(4-Chloro-phenyl)-2,2,4,4-tetramethyl-3-[4-(pyridyl-3)-piperazinyl]-cyclobutanol-(1)

Prepared analogously to Example 1 from 2,2,4,4-tetramethyl-3-[4-(pyridyl-3)-piperazinyl]-cyclobutanone by Grignard reaction with 4-chloro-bromobenzene in ether. Yield: 26% of theory; m.p. 211°–212°C (from isopropanol).

EXAMPLE 120

1-Phenyl-2,2,4,4-tetramethyl-3-[4-(4-amino-pyridyl-3)-piperazinyl]-cyclobutanol-(1)

a. Prepared from 1-phenyl-2,2,4,4-tetramethyl-3-[4-(4-nitropyridyl-(3)-1-oxide)-piperazinyl]-cyclobutanol (m.p. 221°C (decomp.), which had been obtained by condensation of 3-bromo-4-nitropyridine-1-oxide with 1-phenyl-2,2,4,4-tetramethyl-3-piperazinyl-cyclobutanol-(1) (m.p. 184°–185°C), by catalytic hydrogenation with Raney nickel in methanol at room temperature and under hydrogen pressure (5 atmospheres). Yield: 67% of theory; m.p. 286°–289°C (from methanol).

b. Prepared from 1-phenyl-2,2,4,4-tetramethyl-3-[4-(4-aminopyridyl-(3)-1-oxide)-piperazinyl]-cyclobutanol-(1) (m.p. 249°C), which had been obtained from the corresponding nitro-compound (see Example 120a) by catalytic hydrogenation with palladium/carbon at room temperature and under a hydrogen pressure of 5 atmospheres, by catalytic hydrogenation with Raney nickel in methanol at room temperature and under a hydrogen pressure of 5 atmospheres Yield: 76% of theory; m.p. 286°–289°C (from methanol).

EXAMPLE 121

1-Phenyl-2,2,4,4-tetramethyl-3-[4-(4-chloro-pyridyl-3)-piperazinyl]-cyclobutanol-(1)

Prepared from 1-phenyl-2,2,4,4-tetramethyl-3-[4-(4-amino-pyridyl-3)-piperazinyl]-cyclobutanol-(1) by conversion into the diazonium-compound in concentrated hydrochloric acid with sodium nitrite and subsequent decomposition at 30°–40°C. Yield: 67% of theory; m.p. 205°–207°C (from ethyl acetate).

EXAMPLE 122

1-Phenyl-2,2,4,4-tetramethyl-3-[4-(pyridyl-3)-piperazinyl]-cyclobutanol-(1)

Prepared from 1-phenyl-2,2,4,4-tetramethyl-3-[4-(4-chloro-pyridyl-3)-piperazinyl]-cyclobutanol-(1) by catalytic hydrogenation with palladium/carbon in methanol at room temperature and under a hydrogen pressure of 5 atmospheres in the presence of sodium acetate in order to bind the hydrochloric acid splitting off. Yield: 54% of theory; m.p. 211°–214°C (from ethanol).

EXAMPLE 123

1-(4-Isopropyl-phenyl)-2,2,4,4-tetramethyl-3-[4-(4-aminopyridyl-3)-piperazinyl]-cyclobutanol-(1)

a. Prepared from 1-(4-isopropyl-phenyl)-2,2,4,4,-tetramethyl-3-[4-(4-nitro-pyridyl-(3)-1-oxide)-piperazinyl]-cyclobutanol-(1) (m.p. 205°C), which had been obtained by condensation of 3-bromo-4-nitropyridine-1-oxide (m.p. 153°–155°C) with 1-(4-isopropyl-phenyl)-2,2,4,4-tetramethyl-3-piperazinyl-cyclobutanol-(1) (m.p. 207°–212°C), by catalytic hydrogenation with Raney nickel in methanol at room temperature and under a hydrogen pressure of 5 atmospheres. Yield: 74% of theory; m.p. 229°–231°C (from methanol).

b. Prepared from 1-(4-isopropyl-phenyl)-2,2,4,4-tetramethyl-3-[4-(4-amino-pyridyl-(3)-1-oxide)-piperazinyl]-cyclobutanol-(1) (prepared from the corresponding nitro-compound (see Example 123a) by hydrogenation with palladium/carbon at room temperature and at a hydrogen pressure of 5 atmospheres) by catalytical hydrogenation with Raney nickel at room temperature and at a hydrogen pressure of 5 atmospheres. Yield: 76% of theory, m.p. 229°–231°C (from methanol).

EXAMPLE 124

1-(4-Isopropyl-phenyl)-2,2,4,4-tetramethyl-3-[4-(4-chloropyridyl-3)-piperazinyl]-cyclobutanol-(1)

Prepared from 1-(4-isopropyl-phenyl)-2,2,4,4-tetramethyl-3-[4-(4-amino-pyridyl-3)-piperazinyl]-cyclobutanol-(1) by conversion into the diazonium compound in concentrated hydrochloric acid at 0°C with sodium nitrite and subsequent thermical decomposition. Yield: 43% of theory, m.p. 185°–187°C (from ethyl acetate).

EXAMPLE 125

1-(4-Isopropyl-phenyl)-2,2,4,4-tetramethyl-3-[4-(pyridyl-3)-piperazinyl]-cyclobutanol-(1)

Prepared from 1-(4-isopropyl-phenyl)-2,2,4,4-tetramethyl-3-[4-(4-chloro-pyridyl-3)-piperazinyl]-cyclobutanol -(1) by catalytical hydrogenation with palladium carbon in methanol in the presence of sodium acetate for neutralization of the hydrochloric acid formed at room temperature and at a hydrogen pressure of 5 atmospheres. Yield: 56% of theory; m.p. 185°–186°C (from methanol).

EXAMPLE 126

1-Phenyl-2,2,4,4-tetramethyl-3-[4-(pyridyl-4)-piperazinyl]-cyclobutanol-(1)

Prepared from 2,2,4,4-tetramethyl-3-[4-(pyridyl-4)-piperazinyl]-cyclobutanone by Grignard reaction with bromobenzene in tetrahydrofuran analogous to Example 1. Yield: 12% of theory, m.p. 273°–275°C (from chloroform/ethanol).

EXAMPLE 127

1(4-Butyl-phenyl)-2,2,4,4-tetramethyl-3-[4-phenyl-piperazinyl]-cyclobutanol-(1)

Prepared from 2,2,4,4-tetramethyl-3-[4-phenyl-piperazinyl]-cyclobutanone by Grignard reaction with 4-butylbromobenzene in tetrahydrofuran analogous to Example 1. Yield: 55% of theory, m.p. 68°–70°C (from isopropanol).

EXAMPLE 128

DL-1(4-butyl-(2)-phenyl)-2,2,4,4-tetramethyl-3-[4-phenylpiperazinyl]-cyclobutanol-(1)

Prepared from 2,2,4,4-tetramethyl-3-[4-phenyl-piperazinyl]-cyclobutanone by Grignard reaction with DL-4-butyl-(2)-bromobenzene in tetrahydrofuran analogous to Example 1. Yield: 55% of theory, m.p. 107°C (from methanol).

EXAMPLE 129

1-(4-Isobutyl-phenyl)-2,2,4,4-tetramethyl-3-[4-phenyl-piperazinyl]-cyclobutanol-(1)

Prepared from 2,2,4,4-tetramethyl-3-[4-phenyl-piperazinyl]-cyclobutanone by Grignard reaction with 4-isobutylbromobenzene in tetrahydrofuran analogous to Example 1. Yield: 46% of theory, m.p. 101°–102°C (from isopropanol).

EXAMPLE 130

1-(4-Cyclohexyl-phenyl)-2,2,4,4-tetramethyl-3-[4-phenylpiperazinyl]-cyclobutanol-(1)

Prepared from 2,2,4,4-tetramethyl-3-[4-phenyl-piperazinyl]-cyclobutanone by Grignard reaction with 3-cyclohexylbromobenzene in tetrahydrofuran analogous to Example 1. Yield: 62% of theory, m.p. 144°C (from ethanol).

EXAMPLE 131

1-(4-tert.butyl-phenyl)-2,2,4,4-tetramethyl-3-[4-phenylpiperazinyl]-cyclobutanol-(1)

Prepared from 2,2,4,4-tetramethyl-3-[4-phenyl-piperazinyl]-cyclobutanone by Grignard reaction with 4-tert.butylbromobenzene in tetrahydrofuran. Yield: 47% of theory, m.p. 152°C (from ethanol).

EXAMPLE 132

1-(4-n-pentyl-phenyl)-2,2,4,4-tetramethyl-3-[4-phenylpiperazinyl]-cyclobutanol-(1)

Prepared from 2,2,4,4-tetramethyl-3-[4-phenyl-piperazinyl]-cyclobutanone by Grignard reaction with 4-n-pentylbromobenzene in tetrahydrofuran analogous to Example 1. Yield: 29% of theory, m.p. 58°C (from ethanol).

EXAMPLE 133

1-(4-tert.pentyl-phenyl)-2,2,4,4-tetramethyl-3-[4-phenylpiperazinyl]-cyclobutanol-(1)

Prepared from 2,2,4,4-tetramethyl-3-[4-phenyl-piperazinyl] -cyclobutanone by Grignard reaction with 4-tert.pentyl-bromobenzene in tetrahydrofuran analogous to Example 1. Yield: 42% of theory, m.p. 154°–155°C (from petroleum ether).

EXAMPLE 134

1-phenyl-2,2,4,4-tetramethyl-3-[4-(4-nitro-phenyl)-piperazinyl]-cyclobutanol-(1)

Prepared by condensation of 1-phenyl-2,2,4,4-tetramethyl-3-piperazinyl-cyclobutanol-(1) with 4-nitro-chlorobenzene in butanol at the boiling temperature of the solvent. After the solvent has been distilled off, the base was isolated by extraction with chloroform from a basically aqueous solution. Yield: 12% of theory, m.p. 222°–224°C (from ethyl acetate).

EXAMPLE 135

1Phenyl-2,2,4,4-tetramethyl-3-[4-(2-nitro-phenyl)-piperazinyl]-cyclobutanol-(1)

Prepared by reaction of 1-phenyl-2,2,4,4-tetramethyl-3-piperazinyl-cyclobutanol-(1) with 2-nitro-chlorobenzene in butanol at the boiling temperature of the solvent (14 hours). After the solvent has been distilled off, the base was isolated by extraction with chloroform from a basically aqueous solution. Yield: 10% of theory, m.p. 153°–154°C (from methanol).

EXAMPLE 136

1-Biphenylyl-2,2,4,4-tetramethyl-3-[4-phenyl-piperazinyl]-cyclobutanol-(1)

Prepared from 2,2,4,4-tetramethyl-3-[4-phenyl-piperazinyl]-cyclobutanone by Grignard reaction with bromo-biphenyl in tetrahydrofuran analogous to Example 1. Yield: 12.5% of theory, m.p. 148°C (from ethyl acetate).

EXAMPLE 137

1-Phenyl-2,2,4,4-tetramethyl-3-(4-phenyl-piperazinyl)-cyclobutanol-(1) by method C A mixture of 2.8 gm (7.4 millimols) of 3-[bis-(2-chloroethyl)-amino]-2,2,4,4-tetramethyl-1-phenyl-cyclobutanolhydrochloride (crude product, m.p. 60°C, trans-form), 750 mgm (8 millimols) of aniline, 1 spatula tip (a catalytic quantity) of potassium iodide and 20 ml of propanol were refluxed for 17 hours. After addition of 400 mgm (3.7 millimols) of sodium carbonate, the mixture was heated for a further 2½ hours up to the boiling temperature. The reaction mixture was evaporated and 3 N sodium hydroxide solution was added to the residue. After the mixture had been extracted with chloroform, the chloroform layer was washed with water, dried over sodium sulfate and evaporated in vacuo. The crude product was purified by column chromatography with silica gel (eluant: chloroform-/acetone). 150 mgm of a yellow oil was isolated, which was dissolved in a small quantity of isopropanol. After some days 40 mgm of crystals were suction filtered, which are identical to the authentic product except a content of isopropanol. M.p. 123°–125°C (m.p. of the alcohol free substance: 113°C). Yield: 40 mgm (1.5% of theory).

As indicated, the cyclobutane compounds of the general formula I are employed in pharmaceutical compositions customary in the field of sedation and muscle relaxation. The compositions contain a minor amount of the active cyclobutane compounds of the general formula I and a major amount of a pharmaceutical carrier. The pharmaceutical compositions may be in the form of injectable solutions or suspensions, tablets, coated tablets, dragees, sustained release tablets, suppositories, etc. The usual dose is 0.1 to 100 mgm, preferably 0.5 to 5 mgm, and more particularly 1 to 2 mgm, whether administered orally, parentally, or rectally.

EXAMPLE 138

Tablets containing 2 mgm of trans-1-(4-hydroxyphenyl)-2,2,4,4-tetramethyl-3-[4-(pyridyl-2)-piperazinyl]-cyclobutanol-(1) dihydrochloride Composition:
1 Tablet contains:

| | | |
|---|---|---|
| Active ingredient | I | 2.0 mgm |
| Corn starch | II | 65.0 mgm |
| Lactose | III | 48.0 mgm |
| Soluble starch | IV | 4.0 mgm |
| Magnesium stearate | V | 1.0 mgm |
| | Total | 120.0 mgm |

Method of preparation:

Substances I–III were mixed and moistened evenly with an aqueous solution of substance IV. Granulation: moist 1.5 mm; dry 1.0 mm. Substance V was mixed with the mass which was then pressed to tablets. Diameter: 7 mm, punch: flat with facet.

EXAMPLE 139

Coated tablets containing 1 mgm of
trans-1-(4-hydroxyphenyl)-2,2,4,4-tetramethyl-3-[4-
(pyridyl-2)-piperazinyl]-cyclobutan-ol-(1)
dihydrochloride Composition:
1 Coated tablet core contains:

| Active ingredient | I | 1.0 mgm |
|---|---|---|
| Potato starch | II | 25.0 mgm |
| Lactose | III | 20.0 mgm |
| Polyvinylpyrrolidone | IV | 3.0 mgm |
| Magnesium stearate | V | 0.5 mgm |
| | Total | 49.5 mgm |

Method of preparation:

Substances I–III were mixed and moistened evenly with an aqueous solution of IV. Granulation: moist 1 mm, dry 0.75 mm, drying at 50°C. Substance V was mixed with the granulate which was then pressed into tablets with a diameter of 5 mm, Radius of convexity: 3.75 mm. Coating: According to the usual sugar coating. Weight of coated tablet: 80 mgm.

EXAMPLE 140

Suppositories containing 2 mgm of
trans-1-(4-hydroxyphenyl)-2,2,4,4-tetramethyl-3-[4-
(pyridyl-2)-piperazinyl]-cyclobutanol-(1)
dihydrochloride Composition:
1 Suppository contains:

| Active ingredient | 2.0 mgm |
|---|---|
| Suppository mass (e.g. Witepsol H 19 and Witepsol W 45) | 1698.0 mgm |
| Total | 1700.0 mgm |

Method of preparation:

The suppository mass was molten. At 38°C the granulated active ingredient was dispersed homogeneously in the molten mass which was then cooled to 35°C and poured into pre-cooled suppository moulds. Weight of suppository: 1.7 gm.

EXAMPLE 141

Ampules containing 1 mgm of
trans-1-(4-hydroxyphenyl)-2,2,4,4-tetramethyl-3-[4-
(pyridyl-2)-piperazinyl]-cyclobutanol-(1)
dihydrochloride Composition:
1 Ampule contains:

| Active ingredient | 1.0 mgm |
|---|---|
| Sorbitol | 50.0 mgm |
| Distilled water | ad 1.0 ml |

Method of preparation:

The active ingredient and the sorbitol were dissolved in distilled water. The mixture was made up to the indicated volume and filtered sterile. Filling: into brown 1 ml ampules. Sterilization: 20 minutes at 120°C.

EXAMPLE 142

Solution containing 1 mgm of
trans-1-(4-hydroxyphenyl)-2,2,4,4-tetramethyl-3-[4-
(pyridyl-2)-piperazinyl]-cyclobutanol-(1)
dihydrochloride per 5 ml Composition:
100 ml of solution contain:

| Active ingredient | 0.02 gm |
|---|---|
| Carboxymethylcellulose | 0.1 gm |
| Methyl p-hydroxybenzoate | 0.05 gm |
| Propyl p-hydroxybenzoate | 0.01 gm |
| Saccharose | 10.0 gm |
| Glycerin | 5.0 gm |
| Sorbitol solution (70%) | 20.0 gm |
| Aroma | 0.3 gm |
| Distilled water | ad 100.0 ml |

Method of preparation:

Within distilled water heated to 70°C were dissolved while stirring the methyl-p-hydroxybenzoate and the propyl p-hydroxybenzoate as well as the glycerin and the carboxymethylcellulose. The mixture was cooled to room temperature, then the active ingredient was added while stirring. The latter was dissolved, subsequently the saccharose, the sorbitol solution and the aroma were added while stirring and dissolved too. The solution was filtered free of fibers.

As already mentioned above, the new compounds of general formula I possess valuable pharmacological properties, especially a central depressant, sedative, muscle relaxing and anxiolytic activity.

Another aspect of the invention is the method of sedation and relaxing of muscles in warm-blooded animals comprising administering to warm-blooded animals a safe but effective amount of at least one of the compounds of general formula I, alone or in a pharmaceutical composition. The said compounds may be administered orally, parentally or rectally. The usual dosage is from 0.002 to 5 mgm/kg, depending on the method of administration.

EXAMPLE 143

Pharmacological Data

The following substances under the general formula I have been tested according to their biological activity:

A= trans-1-(4-hydroxyphenyl)-2,2,4,4-tetramethyl-3-[4-(pyridyl-2)-piperazinyl]-cyclobutanol-(1) dihydrochloride, B= trans-1-(4-hydroxyphenyl)-2,2,4,4-tetramethyl-3-(4-phenyl-piperazinyl)-cyclobutanol-(1), C= trans-1-(4-hydroxyphenyl)-2,2,4,4-tetramethyl-3-[4-(4-methoxyphenyl)-piperazinyl]-cyclobutanol-(1), D= trans-1-(3,4-dimethoxyphenyl)-2,2,4,4-tetramethyl-3-(4-phenyl-piperazinyl)-cyclobutanol-(1), E= trans-1-(4-hydroxyphenyl)-2,2,4,4-tetramethyl-3-[4-(4-hydroxyphenyl)-piperazinyl]-cyclobutanol-(1), F= trans-1-(4-isopropylphenyl)-2,2,4,4-tetramethyl-3-(4-phenyl-piperazinyl)-cyclobutanol-(1), G= trans-1-(4-isopropylphenyl)-2,2,4,4-tetramethyl-3-[4-(pyridyl-2)-piperazinyl]-cyclobutanol-(1), H= trans-1-(4-chlorophenyl)-2,2,4,4-tetramethyl-3-[4-(pyridyl-2)-piperazinyl]-cyclobutanol-(1), I= trans-1-(4-tert.butylphenyl)-2,2,4,4-tetramethyl-3-[4-(pyridyl-2)-piperazinyl]-cyclobutanol-(1), K= trans-1-(4-tert.butylphenyl)-2,2,4,4-tetramethyl-3-(4-phenyl-piperazinyl)-cyclobutanol-(1), L= trans-D,L-1-(4-butyl-(2)-phenyl)-2,2,4,4-tetramethyl-3-[4-(pyridyl-2)-piperazinyl]-cyclobutanol-(1), M= trans-1-(4-isobutylphenyl)-2,2,4,4-tetramethyl-3-[4-(pyridyl-2)-piperazinyl]-cyclobutanol-(1), N= trans-1-(4-isobutylphenyl)-2,2,4,4-tetramethyl-3-(4-phenyl-piperazinyl)-cyclobutanol-(1),
O= trans-D,L-1-(4-butyl-(2)-phenyl)-2,2,4,4-tetramethyl-3-(4-phenyl-piperazinyl)-cyclobutanol-(1),
P = trans-1-(4-n-butylphenyl)-2,2,4,4-tetramethyl-3-[4-(pyridyl-2)-piperazinyl]-cyclobutanol-(1),
Q= trans-1-(4-n-butylphenyl)-2,2,4,4-tetramethyl-3-(4-phenyl-piperazinyl)-cyclobutanol-(1) and
R= trans-1-(3-chlorophenyl)-2,2,4,4-tetramethyl-3-[4-(pyridyl-2)-piperazinyl]-cyclobutanol-(1).

1. Activity on the spontaneous motility in mice:

The inhibition of spontaneous motility was determined with the aid of photoelectric barriers using an adaption of the method of Friebel, Sommer and Varadan (Arzneimittelforschung 9, 126 (1959)). SPF-NMRI-mice from our own breeding colony, having a body weight between 20 and 26 gm, were used. The number of interruptions in the flow of light was measured by 10 photoelectric cells uniformly distributed in the bottom of a cylindrical cage, 25 cm in diameter, using a counting device. Thus, the spontaneous motility was registered as the animals moved over the bottom of the cage. 5 female mice were placed in each cage and their activity after application of the substance was measured for different periods of time relative to control mice. The present decrease in motility observed after application of various dosages relative to sham treated control animals was determined by graphical extrapolation, so that the dosage necessary for a 50% inhibition of spontaneous motility ($ED_{50}$) could be obtained:

| Substance | 30–45 | $ED_{50}$ mgm/kg p.o. after 90–105 | 150–165 minutes |
|---|---|---|---|
| A | 7.5 | 11 | 6 |
| B | >50 | 3 | 4 |
| C | 11 | 7.5 | 6 |
| D | 26 | 22 | 3 |
| E | 5 | 5 | <2.5 |
| F | 95 | 5 | 2 |
| G | 7 | 3 | 5 |
| H | >13 | 31 | >13 |
| I | 16 | 3 | 3 |
| K | 15 | 3 | 2 |
| L | 7 | 1 | 1 |
| M | 9 | >3 | 0.4 |
| N | 8 | 2 | 1 |
| O | 9 | 3 | 2 |
| P | 9 | 3 | 2 |
| Q | 34 | >3 | 4 |
| R | >25 | 12 | 13 |

2. Muscle relaxing and sedative activity in mice:

The muscle relaxing and sedative activity was tested according to the method of Young and Lewis (Science 105, 368 (1947)) with female NMRI-mice of a specific breed having a body weight of from 20 to 26 gm. The test apparatus comprises slowly turning wire cylinders, sloped for 30° against the vertical line (length: 43 cm; diameter: 22 cm; mesh-size of the wire netting: 0.6 cm). After peroral administration of a suspension of the substance under test in 1% tylose suspension to groups of 10 mice/dose, their bearing in the slowly rotating cylinders (2 rotations/minute) was observed and was compared with a control group. The dose ($ED_{50}$) which caused 50% of the animals to fall out after certain test times was determined graphically:

| Substance | 30–60 | 90–120 | 210–240 | $Ed_{50}$ mgm/kg p.o. after 270–300 minutes |
|---|---|---|---|---|
| A | 5.5 | 7.5 | 8.5 | 7.5 |
| B | 26 | 11 | 6 | 5.5 |
| C | 20 | 16 | 34 | 15.5 |
| D | >40 | 32 | 16 | 14 |
| E | 10 | 13 | 9 | 3 |
| F | 29 | 4 | 2 | 3 |
| G | 11 | 8 | 3 | 8 |
| H | 13 | 22 | 19 | 15 |
| I | 16 | 10 | 17 | 14 |
| K | 48 | 8 | 6 | 1 |
| L | 5 | 4 | 2 | 1 |
| M | 4 | 4 | 3 | 2 |
| N | 65 | 3 | 2 | 3 |
| O | 1 | 1 | 2 | 1 |
| P | 15 | 4 | 3 | 6 |
| Q | >200 | 22 | 8 | 8 |
| R | 46 | 8 | 8 | 11 |

3. Acute Toxicity:

The acute toxicity was determined after oral administration to groups of 10 mice (sex ratio 1:1) from our own breeding colony. The $LD_{50}$ was measured by graphical extrapolation according to the method of Litchfield and Wilcoxon (J. Pharmacol. Exp. Therap. 96, 99 (1949) from the percentage of the animals which died within a period of 14 days after application of various doses:

| Substance | $LD_{50}$ mgm/kg p.o. |
|---|---|
| A | 338 |
| B | 1340 |
| C | >6400 |
| D | 2900 |
| E | >3200 (0 out of 10 animals died) |
| F | >800 |
| G | 118 |
| H | 442 |
| L | 162 |
| O | 800 |

The preceding examples illustrate the practice of the invention. It is to be understood, however, that other expedients known to those skilled in the art or disclosed herein may be employed without departing from the spirit of the invention or the scope of the appended claims.

We claim:

1. A compound of the formula

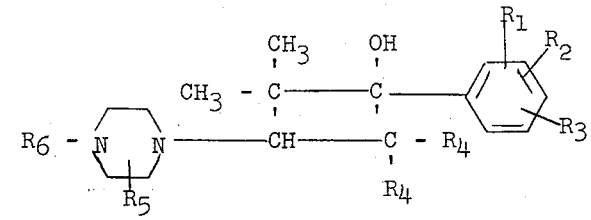

wherein $R_1$ is hydrogen, fluorine, chlorine, bromine, hydroxyl, trifluoromethyl, benzyloxy, alkyl of 1 to 5 carbon atoms, alkoxy of 1 to 3 carbon atoms, benzyloxy, acetoxy, benzoyloxy, isobutyryloxy, phenyl or cyclohexyl, $R_2$ and $R_3$ are each hydrogen, methyl or methoxy, or any two of $R_1$, $R_2$ and $R_3$ taken together are methylenedioxy, $R_4$ is hydrogen or alkyl of 1 to 2 carbon atoms, $R_5$ is hydrogen or methyl, and $R_6$ is

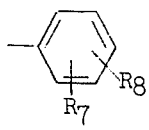 or 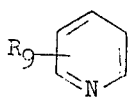

where $R_7$ and $R_8$ are each hydrogen, fluorine, chlorine, bromine, trifluoromethyl, hydroxyl, nitro, benzyloxy, alkyl or 1 to 2 carbon atoms, alkoxy of 1 to 3 carbon atoms, methylthio, acetoxy, benzoyloxy or isobutyryloxy, and $R_9$ is hydrogen, chlorine, bromine, hydroxyl, nitro, amino, benzyloxy, carboxy, carbomethoxy, carbethoxy, methyl, methoxy or acetoxy, provided however, that only one of $R_1$, $R_7$, $R_8$ and $R_9$ is acetoxy, benzoyloxy or isobutyryloxy; a physiologically compatible acid addition salt thereof; or, when $R_9$ is carboxy, a physiologically compatible salt thereof formed with an inorganic or organic base.

2. A cyclobutane derivative of claim 1 wherein the transconfiguration is present.

3. A trans-cyclobutane derivative of claim 2, wherein $R_1$, $R_2$, $R_3$ and $R_5$ are hydrogen, $R_4$ is methyl, and $R_6$ is phenyl, 4-hydroxyphenyl, 4-methoxyphenyl or pyridyl-2.

4. A trans-cyclobutane derivative of claim 3, which is trans-1-(4-isopropylphenyl)-2,2,4,4-tetramethyl-3-[4-(pyridyl-2)-piperazinyl]-cyclobutanol-(1) or a physiologically compatible acid addition salt thereof.

5. A trans-cyclobutane derivative of claim 3, which is trans-1-(4-isopropylphenyl)-2,2,4,4-tetramethyl-3-(4-phenyl-piperazinyl)-cyclobutanol-(1) or a physiologically compatible acid addition salt thereof.

6. A trans-cyclobutane derivative of claim 3, which is trans-1-(4-chlorophenyl)-2,2,4,4-tetramethyl-3-[4-(pyridyl-2)-piperazinyl]-cyclobutanol-(1) or a physiologically compatible acid addition salt thereof.

7. A trans-cyclobutane derivative of claim 3, which is trans-1-(4-tert.pentylphenyl)-2,2,4,4-tetramethyl-3-[4-(pyridyl-2)-piperazinyl]-cyclobutanol-(1) or a physiologically compatible acid addition salt thereof.

8. A trans-cyclobutane derivative of claim 3, which is trans-D,L-1-(4-butyl-(2)-phenyl)-2,2,4,4-tetramethyl-3-[4-(pyridyl-2)-piperazinyl]-cyclobutanol-(1) or a physiologically compatible acid addition salt thereof.

9. A trans-cyclobutane derivative of claim 3, which is trans-D,L-1-(4-butyl-(2)-phenyl)-2,2,4,4-tetramethyl-3-(4-phenyl-piperazinyl)-cyclobutanol-(1) or a physiologically compatible acid addition salt thereof.

10. A trans-cyclobutane derivative of claim 3, which is trans-1-(4-hydroxyphenyl)-2,2,4,4-tetramethyl-3-[4-(pyridyl-2)-piperazinyl]-cyclobutanol-(1) or a physiologically compatible acid addition salt thereof.

11. A trans-cyclobutane derivative of claim 3, which is trans-1-(4-propylphenyl)-2,2,4,4-tetramethyl-3-[4-(pyridyl-11) or a physiologically compatible acid addition salt thereof.

* * * * *

UNITED STATES PATENT OFFICE
CERTIFICATE OF CORRECTION

Patent No. 3,931,185　　　　　　　　　　Dated January 6, 1976

Inventor(s) MANFRED KLEEMAN, JOACHIM KAHLING, GERHART GRISS and RUDOLF HURNAUS

It is certified that error appears in the above-identified patent and that said Letters Patent are hereby corrected as shown below:

In Col. 21, Line 67　　"power" should read -- powder --

In Col. 34, Line 28　　"-(pyridyl-11)" should read -- -(pyridyl-2)-piperazinyl]-cyclobutanol-(1) --

Signed and Sealed this twenty-third Day of March 1976

[SEAL]

Attest:

RUTH C. MASON
Attesting Officer

C. MARSHALL DANN
Commissioner of Patents and Trademarks